United States Patent [19]

Metrich

[11] Patent Number: 5,312,538
[45] Date of Patent: May 17, 1994

[54] DEVICE FOR CONTROLLING THE ELECTRICAL POWER SUPPLY OF AN OXYGEN PUMP OF A LINEAR OXYGEN PROBE

[75] Inventor: Pierre M. R. Metrich, Plaisance du Touch, France

[73] Assignee: Siemens Aktiengesellschaft, Munich, Fed. Rep. of Germany

[21] Appl. No.: 613,080

[22] Filed: Nov. 14, 1990

[30] Foreign Application Priority Data

Nov. 14, 1989 [FR] France ................... 8914891

[51] Int. Cl.⁵ .......................................... G01N 27/419
[52] U.S. Cl. ................................ 204/425; 204/153.18; 204/406
[58] Field of Search ............... 204/153.18, 421–429, 204/406

[56] References Cited

U.S. PATENT DOCUMENTS 3,992,622  11/1976  Numata et al. ................. 328/145
4,759,328  7/1988  Blumel et al. ................... 123/440

FOREIGN PATENT DOCUMENTS 0025625  3/1981  European Pat. Off. .
0079085  5/1983  European Pat. Off. .
0194082  9/1986  European Pat. Off. .
0266501  5/1988  European Pat. Off. .
2552863  5/1976  Fed. Rep. of Germany .

OTHER PUBLICATIONS

Hetrick et al., "Oscillatory-Mode Oxygen Sensor", 8093 IEEE Transactions on Electron Devices, vol. ED-29 (1982), Jan., No. 1, New York, USA, pp. 129–132.

Primary Examiner—T. Tung
Attorney, Agent, or Firm—Hill, Steadman & Simpson

[57] ABSTRACT

A device for controlling electrical power to an oxygen pump portion of a linear oxygen sensor comprises a bridge of transistors controlled by a microprocessor. The microprocessor processes a measurement signal delivered by a measurement cell of the probe in order to control the direction and duration of the passage through an oxygen pump of a current of predetermined strength, the current being controlled based on the measurement signal. The current is periodically alternated, and provided with a variable cyclic ratio, by appropriate switching of the transistors in the bridge. The device is used for the measurement of the air/fuel ratio in the mixture supplied to an internal combustion engine.

11 Claims, 2 Drawing Sheets

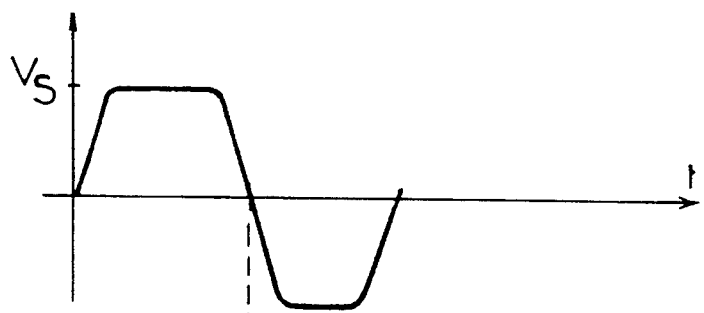
FIG. 2A
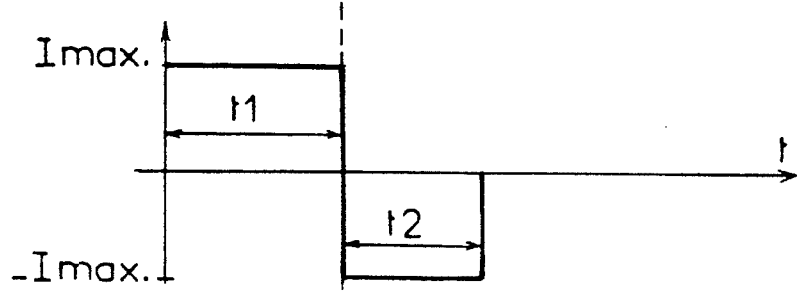
FIG. 2B
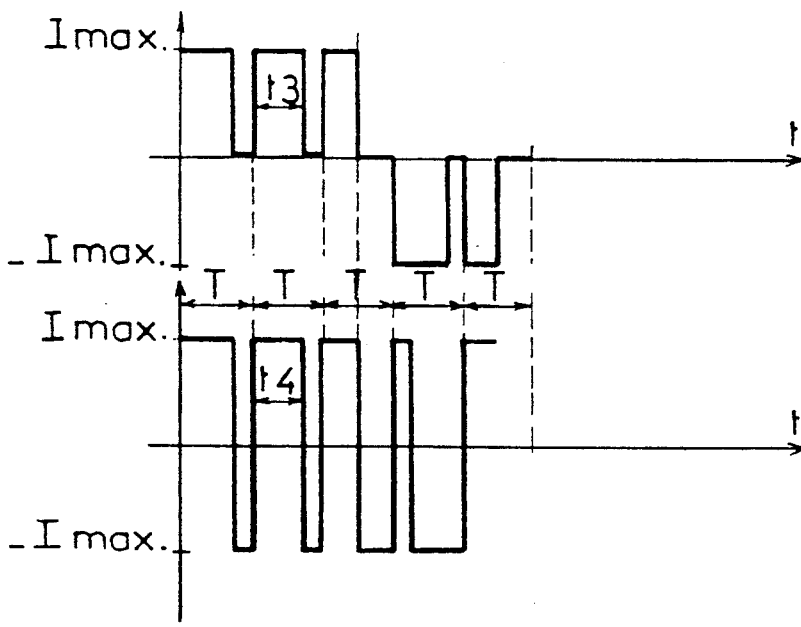
FIG. 2C
FIG. 2D
FIG. 3
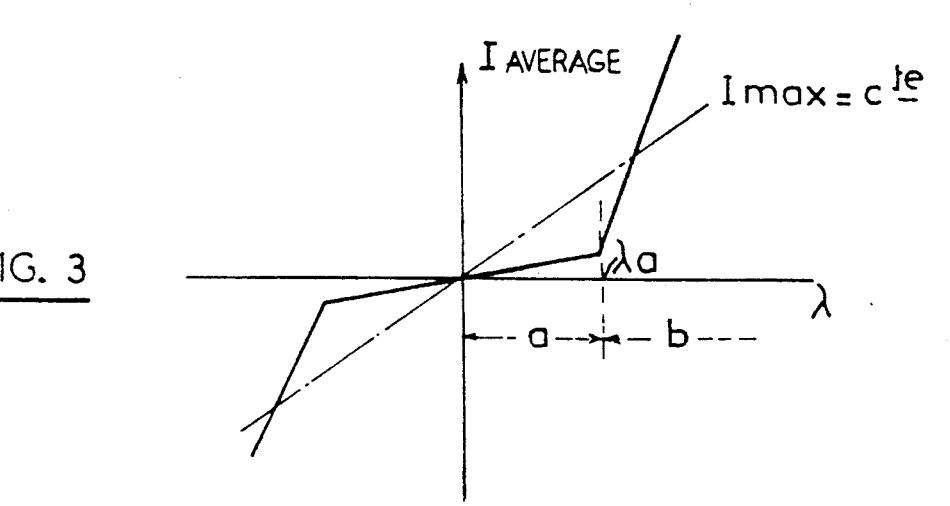

DEVICE FOR CONTROLLING THE ELECTRICAL POWER SUPPLY OF AN OXYGEN PUMP OF A LINEAR OXYGEN PROBE

BACKGROUND OF THE INVENTION

1. Field of the Invention

The present invention relates to a device for the controlling electrical power supply to an oxygen pump forming part of a linear oxygen probe apparatus and, more particularly, to such a device for measuring the oxygen concentration in exhaust gases from an internal combustion engine.

2. Description of the Related Art

It is known that an important parameter in the operation of an internal combustion engine is the air coefficient lambda ($\lambda$) which represents the air:fuel ratio in the mixture supplied to the engine divided by the ratio corresponding to a stoichiometric mixture. The importance of this parameter comes from its effect on the engine power, on the engine's specific consumption and, above all, on the composition of the exhaust gases from the engine, particularly noxious gases. Antipollution laws of ever greater severity oblige engineers to provide for regulation of this coefficient $\lambda$, making it possible to obtain as complete a combustion of the mixture as possible.

To this end, the composition of the latter is measured indirectly by detection of the amount of oxygen present in the exhaust gases. Given that these gases contain oxygen even when the mixture is "rich" ($\lambda<1$), the measurement of this amount of oxygen enables the composition of the mixture supplied to the engine to be measured.

For this purpose, a sensor known as an "oxygen probe" or "lambda probe" is used, the probe being placed in the flow of exhaust gases from the engine. Conventionally, such a probe consists of a mass of zirconium or titanium oxide placed between two electrodes, with one of the electrodes being exposed to the exhaust gases through a protective layer of porous ceramic while the other electrode is in contact with the open air. A voltage is observed between the electrodes which is a function of the difference in the oxygen ion concentration between the two electrodes. In particular, a jump in voltage is observed at around $\lambda=1$, due to the particular properties of the material used, whether zirconium oxide or titanium oxide.

As a result of this jump, such a probe supplies a signal which in practice takes on only two states, representative of a mixture in which either $\lambda<1$ or $\lambda>1$. It is, therefore, impossible to measure the real departure of the mixture from its stoichiometric composition.

To overcome this drawback, an oxygen probe described as "linear" has been designed which is capable of supplying a signal which is substantially linearly proportional to the coefficient $\lambda$ both above and below the stoichiometric composition.

Such a linear oxygen probe normally comprises, as represented in a portion of FIG. 1 of the appended drawing, a measurement cell 1 and an oxygen pump 2 separated by a measurement cavity 3, the measurement cell 1 being itself bounded on its other face by a reference cavity 4. The measurement cell 1 consists of a standard oxygen probe comprising a body 5 made of zirconium or titanium oxide, for example, and two electrodes 6 and 7 placed against this body, in the measurement cavity 3 and in the reference cavity 4, respectively. The measurement cell delivers a voltage $V_s$ across these electrodes which depends on the amount of oxygen present in the measurement cavity. The measurement cavity 3 is in communication with the exhaust gases from the engine, as is a volume 8 which surrounds an electrode 9 of the oxygen pump whose other electrode 10 lies in the measurement cavity 3. The oxygen pump 2 comprises, like the measurement cell 1, a mass of zirconium or titanium oxide placed between the electrodes 9 and 10.

Passing a current $I_p$ through the oxygen pump 2 causes oxygen to arrive in the measurement cavity 3 or causes it to be extracted from this cavity 3, depending on the direction of the current. By bringing this current and its direction under the control of the voltage $V_s$ delivered by the measurement cell 1, a closed loop regulation of the oxygen concentration in the measurement cavity 3 is ensured by a supply of oxygen to, or a withdrawal of oxygen from, this cavity depending on the oxygen concentration in the exhaust gases entering this cavity. The current $I_p$ is then a substantially linear function of this oxygen concentration and, thus, of the coefficient $\lambda$ representative of the composition of the air-fuel mixture. As an example of a known probe which operates according to this principle, the probe sold under the name NTK UEGO by the Japanese company NGK SparkPlug Co. Ltd may be cited.

The problem is then to bring the current $I_p$ supplied to the pump under the control of the voltage $V_s$ delivered by the measurement cell. For this purpose, use is conventionally made of a complex PID-type analog circuit consisting of many analog amplifiers and precision components. Such an analog circuit is subject to drifting. Its complexity and the presence of precision components make the cost prohibitive. Moreover, since the functioning of the feedback control is fixed by the structure of the circuit, this functioning cannot be modified by using various strategies programmed in advance, as is the case with digital systems controlled by a microprocessor, for example.

SUMMARY OF THE INVENTION

The present invention therefore has as an object the production of a device for the electrical power supply of an oxygen pump forming part of a linear oxygen probe which does not have these drawbacks.

More particularly, the invention has as an object the production of such a device which has a simple structure with a small number of components, which is reliable and cheap to produce.

The present invention also has as an object the production of such a device making it possible to ensure the precise regulation of the current supplied to the oxygen pump, with correction for drifts in temperature.

The present invention has as yet another object the production of such a device incorporating means for enabling its operation to be controlled according to various strategies.

These objects of the invention are achieved, together with others which will emerge in the remainder of the present description, with a device for the electrical power supply of an oxygen pump forming part of a linear oxygen probe used for the measurement of the oxygen concentration in the exhaust gases from an internal combustion engine, this probe comprising in addition a measurement cell that is sensitive to the amount of oxygen present in a measurement cavity of the probe, the measurement cavity being in communication with the exhaust gases and with the oxygen pump in order to deliver a corresponding measurement signal. The measurement signal is used to control the electrical power supply to this pump. According to the invention, the device further comprises, in combination, (a) a source of electrical energy and (b) means for connecting this source selectively to the oxygen pump in such a way as to provide to the pump a periodic alternating electrical supply of current of predetermined strength and with a variable cyclic ratio that is controlled by the measurement signal delivered by the measurement cell.

According to one characteristic of the present invention, the means comprise an "H" bridge of transistors consisting of two pairs of transistors, the emitter-collector circuits of the transistors in each pair being connected in series. The oxygen pump is connected between the transistor terminals that are common to the emitter-collector circuits of the transistors of each pair, and the pairs of emitter-collector circuits in series are each connected between the source of electrical energy and ground.

The means also comprise means for selectively and individually controlling the conducting state of the transistors in the bridge in such a way that the sign of the average current through the pump is reversed after each switch-over of the measurement signal.

In each pair of transistors of the bridge, the transistors of a preferred embodiment are of opposite types, and the means for controlling the conducting state of the transistors simultaneously blocks one transistor of each pair and unblocks the other transistor by a control common to their bases. The controls of the two pairs of transistors are determined by the measurement signal in order to control the direction and duration of the passage of the current produced by the source of electrical energy through the oxygen pump. Of course, it is also possible to provide substantially simultaneous blocking and unblocking of the transistors by other means, such as through the use of inverters.

The means for selective connection of the source of electrical energy to the oxygen pump are designed so as to be able to put into operation several different strategies, or programs, for controlling the electrical supply to this oxygen pump.

BRIEF DESCRIPTION OF THE DRAWINGS

Other characteristics and advantages of the present invention will emerge on reading the description which follows and on examining the appended drawing in which:

FIGS. 2A and 2D represent various waveforms useful in the description of various strategies for controlling the current through the oxygen pump, and FIG. 3 is a graph illustrating another strategy for regulating the current through the oxygen pump.

DESCRIPTION OF THE PREFERRED EMBODIMENTS

Figure 1:
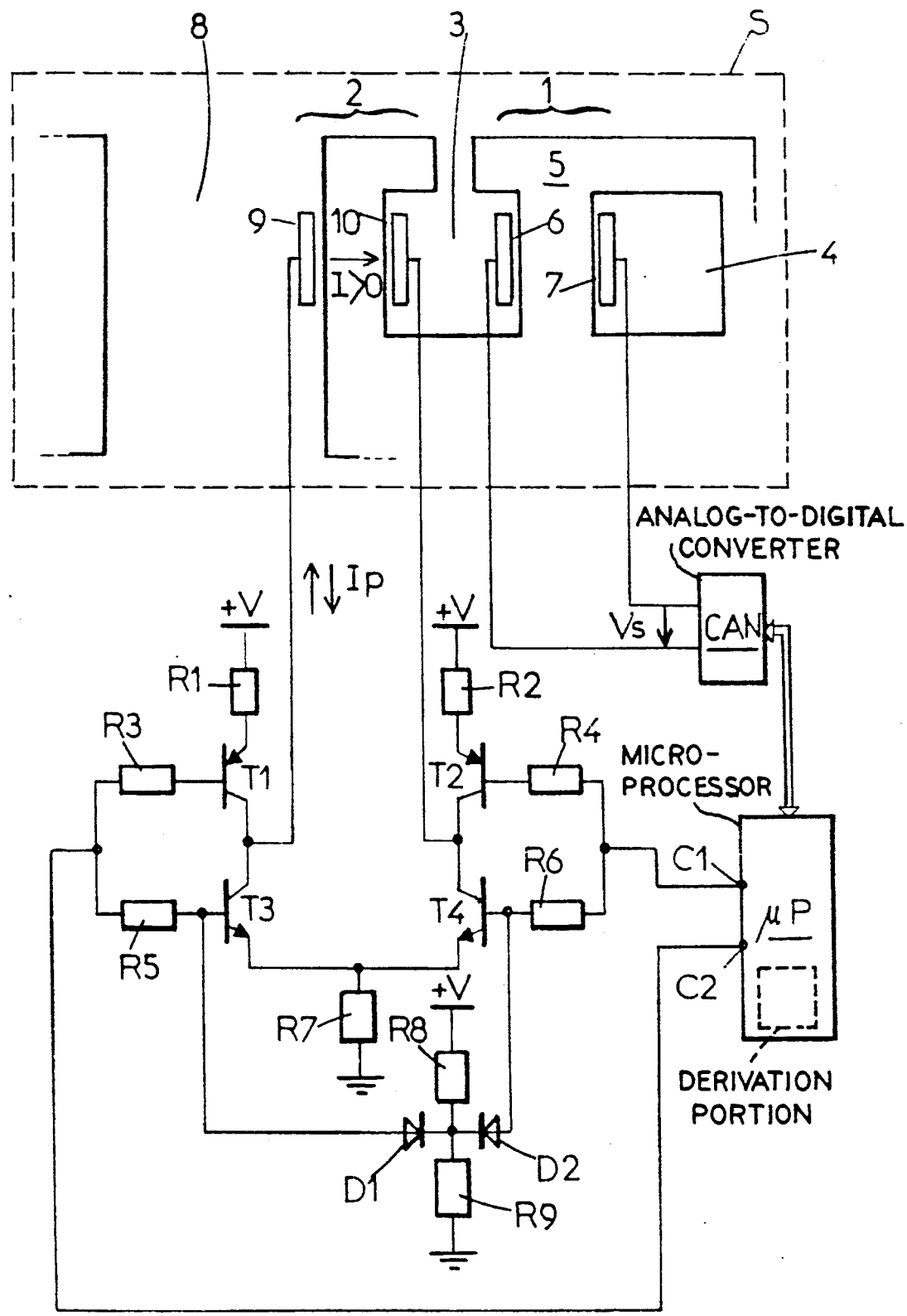
FIG. 1 is a diagram of the device for the electrical power supply of an oxygen pump forming part of a linear oxygen probe of the type described in the preamble to the present description.

Reference is made to FIG. 1 in the appended drawing, which is a diagrammatic representation of the linear oxygen probe described in the preamble to the present description.

FIG. 1 also represents the device for the electrical power supply of the oxygen pump of the probe according to the present invention. This device consists essentially of a source of electrical energy delivering a voltage $+V$ and of means for selectively connecting this source in series with the electrodes 9 and 10 of the oxygen pump 2 in such a way as to bring the direction and the duration of the passage of a current $I_p$ of predetermined strength through the pump under the control of the measurement signal $V_s$ delivered by the measurement cell 1. These means comprise essentially an "H" bridge of transistors T1 and T2, T3 and T4 and a microprocessor $\mu P$ selectively controlling the conduction of the transistors in the bridge by signals emitted at output pins C1 and C2. The microprocessor $\mu P$ is itself supplied with the output signal $V_s$ from the measurement cell 1 through an analog-to-digital convertor CAN. Within the microprocessor may be considered a derivation portion which derives the $\mu P$ signals on the output pins C1 and C2 from the converted measurement signal.

The microprocessor $\mu P$ is duly programmed in order to emit from the pins C1 and C2 signals making it possible to adjust the average current of the pump 2 in such a way as to regulate the oxygen concentration in the measurement cavity 3 and hence the value of the output voltage $V_s$ from the measurement cell 1. This regulation is implemented by the extraction of oxygen from the measurement cavity 3 under the action of the oxygen pump 2.

Thus, when the oxygen concentration in the exhaust gas from an internal combustion engine (which fills the cavities 8 and 3 of the probe) is representative of an air/fuel mixture supplied to the engine characterized by an air coefficient $\lambda > 1$, there is an extraction of oxygen from the cavity 3 under the action of the pump through a suitable adjustment of the current $I_p$ by the device according to the invention, as will be seen in what follows, so as to bring the oxygen concentration in the cavity 3 back to a value corresponding to $\lambda = 1$. Conversely, if the oxygen concentration corresponds to an air coefficient $\lambda < 1$, oxygen is pumped into the cavity 3 by the oxygen pump being excited by a current $I_p$ with a direction which is the reverse of the current used in extracting oxygen from this cavity. In this way, the current $I_p$ through the oxygen pump is representative of the difference between the composition of the air/fuel mixture and the composition corresponding to $\lambda = 1$. The variation of $I_p$ as a function of this difference is substantially linear.

According to the known devices, $I_p$ is adjusted by complicated PID-type analog circuits. The present invention provides instead a digital control for this current, which is simpler and more flexible, as will be seen later.

To this end, the "H" bridge of the transistors T1, T2, T3 and T4 is designed to provide a switching of the direction of the current $I_p$ in the oxygen pump, under the control of signals emitted at the pins C1 and C2 of the microprocessor $\mu P$. The bridge consists of two pairs of bipolar transistors T1 and T3 on the one hand and T2 and T4 on the other. The respective transistors of the same pair are of opposite types. Thus, the transistors T1 and T2 are of the PNP type, for example, while the transistors T3 and T4 are of the NPN type.

In each pair, the emitter-collector circuits of the two transistors are connected in series between a line at the supply voltage $+V$ and ground. The common terminals of the emitter-collector circuits of the transistors T1 and T3, on the one hand, and of T2 and T4, on the other, are connected respectively to the electrodes 9 and 10 of the oxygen pump 2. Load resistors R1 and R2 are connected to the emitters of the transistors T1 and T2, respectively, between the latter and the line at the supply voltage +V. The emitters of the transistors T3 and T4 are connected to each other and their common point is connected to ground through an grounding resistor R7. The bases of the transistors T1, T3, T2 and T4 are loaded by resistors R3, R5, R4 and R6, respectively. The points common to the resistors R4 and R6, on the one hand, and to R3 and R5, on the other, are connected to the pins C1 and C2, respectively, of the microprocessor μP.

The device also comprises a generator of a reference voltage consisting of two resistors R8 and R9 placed in series between the line at +V and ground. The central point of the voltage divider formed in this way is connected to the bases of the transistors T3 and T4. Diodes D1 and D2, connected in a forward-biased configuration between the bases of T3 and T4, respectively, and the central point of the voltage divider R8 and R9, provide a compensation of the variations in the base-emitter voltages $V_{be}$ of the transistors T3 and T4 due to temperature variations, for a purpose that will be explained later.

With the circuit which has just been described, it is clear that if, for example, the microprocessor μP establishes a zero voltage on its pin C1, the transistor T4 is blocked, whereas the transistor T2 is saturated. In this way, the voltage +V is applied, through the resistor R2 and the emitter-collector circuit of the transistor T2, to the electrode 10 of the oxygen pump. If, in addition, the microprocessor simultaneously establishes on its pin C2 a voltage $V_1$ of suitable magnitude, this voltage causes the blockage of the transistor T1 of the other pair of transistors T1 and T3 and the unblocking of the transistor T3. The electrode 9 of the oxygen pump 2 is then connected to ground through the collector-emitter circuit of the transistor T3 and the grounding resistor R7. In this way, a potential difference is set up between the electrodes 9 and 10 of the oxygen pump and a current $I_p$ flows in the pump in the direction opposite to that of the arrow shown between the electrodes 9 and 10, which denotes a direction for the current chosen arbitrarily as the positive direction. The current which then passes into the probe is that which, having passed through the resistor R2 and the transistor T2, flows to ground through the transistor T and the fixed resistor R7. It is clear that the strength I of the current in this circuit is then determined by the bias of the base of the transistor T3, which then functions as a current generator, i.e. by the voltage at the central point of the divider bridge R8 and R9. In this connection, it will be noted that the diode D1 compensates for any variation with temperature of the voltage $V_{be}$ of the transistor T3 in order to prevent in this way a drift of the bias voltage of this transistor, and thus to maintain the current $I_p$ at a predetermined value.

It is clear that, by reversing the voltages set up above on the pins C1 and C2 of the microprocessor, the direction of the current in the oxygen pump 2 is also reversed. Similarly, by applying equal or zero voltage signals to the pins C1 and C2, any passage of current through the oxygen pump is cut off. The table below compiles the various situations mentioned above.

| Voltages on pins | State of the bridge | Current I in pump 2 |
|---|---|---|
| C1 = $V_1$ | T4 conducts T2 blocked | i = 0 |
| C2 = $V_1$ | T3 conducts T1 blocked | |
| C1 = 0 | T4 blocked T2 saturated | I < 0 imposed |
| C2 = $V_1$ | T3 conducts T1 blocked | by current generator |
| C1 = $V_1$ | T4 conducts T2 blocked | I > 0 imposed |
| C2 = 0 | T3 blocked T1 saturated | by current generator |
| C1 = 0 | T4 blocked T2 saturated | I = 0 |
| C2 = 0 | T3 blocked T1 saturated | |

It can thus be seen that, according to the invention, it is possible to fix both the direction and duration of the passage through the pump 2 of a current of predetermined strength I. Also according to the invention, the microprocessor μP is duly programmed to emit at the pins C1 and C2 control signals enabling the average current passing through the oxygen pump 2 to be brought under the control of the measurement signal $V_s$ digitized by the convertor CAN. As a result of such control, the average value of the current is, at each instant, representative of the air coefficient λ of the air/fuel mixture supplied to the internal combustion engine. The maximum value Imax of the current passing through the pump is fixed by the voltage divider R8 and R9, the measurement resistor R7 and the supply voltage +V of the bridge of transistors T1, T2, T3 and T4. Because the diodes D1 and D2 exactly compensate the variations with temperature of the voltages $V_{be}$ of the transistors T3 and T4, the current I through the oxygen pump 2 has almost the same absolute value Imax in both of the directions in which this current flows. Thus, by applying appropriate signals to the pins C1 and C2, the microprocessor can adjust with precision the average current passing through the pump between two values +Imax and −Imax. Various strategies are then possible for bringing this current under the control of the voltage signal $V_s$.

According to a first strategy, illustrated in FIG. 2B, the microprocessor measures the successive times t1, t2, etc. necessary to make the voltage $V_s$ (see FIG. 2A) switch over when the oxygen pump is supplied with a current of strength I=Imax. These times are then a function of λ. However, this strategy has several drawbacks. Firstly, the inertia of the probe is such that the measured time t2 suffers from an overshoot in the previous time t[1], (see FIG. 2B, in correlation with the switchovers of the signal $V_s$ represented in FIG. 2A). Secondly, the measurement depends on the precision of the adjustment in the value of Imax. Finally, around λ=1, the times to be measured become very short, which entails a reduction in the precision of the measurement just where it is most needed.

According to a second strategy illustrated in FIG. 2C, the means adopted for selectively connecting the source of electrical energy to the oxygen pump 2 provide a periodic supply with a variable cyclic ratio to the pump of a predetermined current Imax whose direction is reversed at each switchover of the measurement signal $V_s$. Since the control signal has a period T, the average current over a period during which the current Imax is applied for a time $t_3$ has the form:

$$I_{average} = t_3/T \times Imax, \text{ if } V_s \text{ is positive}$$

$$I_{average} = t_3/T \times (-Imax), \text{ if } V_s \text{ is negative.}$$

This strategy has the drawback that it makes the measurement of $I_{average}$ depend on the precision of $+I_{max}$ and $-I_{max}$. Moreover, near $\lambda=1$, the cyclic ratios are small because the time $t_3$ is very much less than T. Certain periods might even pass by in their entirety with a zero current, which impairs the speed and precision of the measurements.

The graph of FIG. 2D illustrates a preferred control strategy of the device according to the present invention. According to this strategy, the means for selectively connecting the source of electrical energy to the oxygen pump provide an alternating periodic supply with a variable cyclic ratio, the sign of the average current being reversed after each switchover of the measurement signal $V_s$. Thus, referring to FIG. 2D, over a period during which a current $+I_{max}$ has been applied for a time $t_4$, we have:

$$I_{average} = I_{max} \times t_4 T - I_{max} \times (T - t_4))/T$$

or, with acyclic ratio $r = r_4/T$, $$I_{average} = I_{max} \times (2r - 1).$$

Near $\lambda=1$, $I_{average}$ must be small, with the cyclic ratio r then becoming established at about 50%. Because Imax and -Imax are fixed by the same voltage divider R8 and R9, an error in Imax is compensated by the same error in (−Imax), and the final measurement of $\lambda$ that is obtained does not depend on the precision in the maximum strength of the current delivered by the device according to the invention, which is an undoubted advantage of the strategy described above.

All the strategies mentioned so far have worked with values of Imax fixed in absolute value. It is also possible to make this parameter vary, for example, as a function of the range that occurs in the richness of the air/fuel mixture, in order to increase the dynamic range of the measurement. It is easy to obtain, with the control by a microprocessor, a variation in Imax by switching between several resistors R7 or several divider bridges R8 and R9, for example. The graph of FIG. 3 illustrates the variation of the average current through the oxygen pump as a function of $\lambda$ when Imax is switched over a greater value when $\lambda$ changes to the value a. Over the region a, near $\lambda=1$, it is possible to obtain a high resolution since the ratio of variations $\Delta I_{average}/\Delta r$ is small. On the other hand, in the region b which extends beyond the region a, it is possible to have a large dynamic range since the ratio $\Delta I_{average}/\Delta r$ is high.

It is now evident that the device for the power supply of the oxygen pump of a linear oxygen probe according to the invention has many advantages. Firstly, the device has great simplicity and contains a small number of components, which has a beneficial effect on its manufacturing cost.

The precision of the measurements that are obtained is high because only the three resistors R7, R8 and R9 and the voltage $+V$ affect the initial precision of the device. Moreover, since the latter is controlled by a microprocessor, this imprecision can be compensated by a numerical calibration consisting in storing in the microprocessor correction parameters as a function of the observed initial drift.

The temperature drift of the circuit is very small because of the compensation of the voltages $V_{be}$ of the transistors T3 and T4 by the diodes D1 and D2, such a temperature drift depending on no more than the differential drift of the resistors, on the voltage V and on the differential variation in the gains of the transistors.

The device is reliable since the circuit is self-protected against short circuits to ground thanks to the limitations of current established by the resistors R1 and R2, and against short circuits of the power supply, constituted generally by the battery of the vehicle in automobile electronics.

The device according to the invention also possesses a great flexibility in operation because a microprocessor is used to ensure the control of the probe and because this microprocessor can be programmed in such a way as to establish one or another of several control strategies of varying degrees of sophistication.

It is known that an oxygen probe must be fitted with means of heating since the signal provided is only reliable above a certain temperature, for example of the order of 200° C. Since the microprocessor can also carry out the control of the heating of the probe and the measurement of the signal $V_s$ delivered by this probe, this microprocessor can thus ensure the control of the whole system.

Of course, the invention is not limited to the embodiment described and illustrated, which has only been given as an example. In particular, the invention is not limited to a device produced with bipolar technology and could just as easily be produced with MOS technology, for example.

Although other modifications and changes may be suggested by those skilled in the art, it is the intention of the inventor to embody within the patent warranted hereon all changes and modifications as reasonably and properly come within the scope of his contribution to the art.

I claim:

1. A device for supplying electrical power to an oxygen pump of a linear oxygen probe for measuring oxygen concentration in exhaust gases from internal combustion engines, comprising:
    an oxygen pump of a linear oxygen probe including a pair of electrodes;
    a measurement cavity of the probe in communication with exhaust gases and with said oxygen pump;
    a measurement cell in communication with said measurement cavity, said measurement cell being sensitive to oxygen present in said measurement cavity of the probe to produce a corresponding measurement signal;
    an electrical power supply of the oxygen pump connected for control by the measurement signal, said power supply including:
    a source of electrical energy; and
    means for selectively connecting said source to said pair of electrodes of said oxygen pump so as to provide a current of alternating electrical strength of a fixed frequency and of variable cyclic ratio controlled by said measurement signal from said measurement cell, said fixed frequency being higher than a frequency of said measurement signal, said current being independent of oxygen concentration, said variable cyclic ratio being a measure of the oxygen concentration.

2. A device as claimed in claim 1, wherein said means for selectively connecting comprises:
    a resistor;
    an H bridge of transistors including
    four transistors grouped in two pairs wherein each of said pairs have their emitter-collector circuits connected in series, each of said pairs being connected between said source of electrical energy and in common to said resistor to ground, each of said pairs having a connection to said oxygen pump between commonly connected terminals of said transistors so that said commonly connected terminals of one pair are connected to said commonly connected terminals of the other pair through said oxygen pump, each of said pairs of transistors of said bridge being two transistors of opposite types, means for selectively and individually controlling conduction of said transistors in said bridge so that a sign of an average current through said pump is reversed after each switch-over of the measurement signal, said means for controlling simultaneously blocking one transistor of each pair and unblocking another transistor of each pair by common control of their bases, said means for controlling including means for controlling said two pairs of transistors depending on the measurement signal so that current from said source of electrical energy through the oxygen pump is controlled;

a reference voltage generator connected to said base of one of said transistors of each of said pair of transistors to control current strength through the oxygen pump.

3. A device as claimed in claim 2, wherein said means for controlling includes an analog to digital converter connected to convert the measurement signal to a digital signal, and a microprocessor connected to receive the converted measurement signal from said analog-to-digital converter, said microprocessor including means for deriving two transistor control signals from the converted measurement signal to control said pairs of transistors, said microprocessor including means for storing parameters for correcting an initial drift in a component of the device, said component being at least one of said resistor and elements of said reference voltage generator;

means for connecting said two transistor control signals to said two pairs of transistors so that said transistors control the existence and direction of current flow through the oxygen pump; and means for storing parameters of an initial calibration of the device.

4. A device as claimed in claim 2, wherein said reference voltage generator includes a voltage divider having a central point connected to said base of said one transistor of each of said pairs of transistors, and diodes connected between said voltage divider and said one transistor of each of said pairs of transistors to compensate for temperature variations of base-emitter voltages of said transistors.

5. A device as claimed in claim 1, further comprising: means for selectively varying current strength flowing through the oxygen pump.

6. A power control circuit for controlling electrical energy from a voltage source, comprising:

a linear oxygen probe having an oxygen pump, the oxygen pump being connected to receive electrical energy from the voltage source, the oxygen probe having an output producing a measurable signal;

means for supplying a periodically alternating signal to said oxygen pump; and means for varying a cyclic ratio of said periodically alternating signal depending on a value of said measuring signal.

7. A power control circuit as claimed in claim 6, wherein said means for supplying includes:

a first pair of transistors having their emitter-collector terminals connected in series between the voltage source and ground;

a second pair of transistors having their emitter-collector terminals connected in series between the voltage source and ground; and means for connecting commonly connected terminals of each of said first and second pair to said oxygen pump.

8. A power control circuit as claimed in claim 7, wherein said means for varying includes a microprocessor having an input connected to receive said measuring signal and outputs connected to said first and second pairs of transistors.

9. A power control circuit as claimed in claim 7, wherein said means for supplying includes a voltage divider having an intermediate connection connected to one of said transistors of each of said first and second pairs of transistors.

10. A power control circuit as claimed in claim 9, further comprising:

first and second diodes connected between said intermediate connection of said voltage divider and respective ones of said transistors of each of said first and second pairs of transistors.

11. A power control circuit as claimed in claim 7, wherein said first pair of transistors comprise an npn transistor and a pnp transistor, and said second pair of transistors comprise an npn transistor and a pnp transistor, said transistors of said first pair being connected to said means for varying so that said first pair of transistors are switched substantially opposite one another and said transistors of said second pair being connected to said means for varying so that said second pair of transistors are switched substantially opposite one another.

* * * * *